(12) United States Patent
Poissonnier-Durieux et al.

(10) Patent No.: US 7,214,689 B2
(45) Date of Patent: May 8, 2007

(54) ISOQUINOLINE COMPOUNDS

(75) Inventors: Sophie Poissonnier-Durieux, Rainneville (FR); Valérie Wallez, Wervicq-Sud (FR); Anne Gasnereau, Lille (FR); Said Yous, Loos (FR); Daniel Lesieur, Gondecourt (FR); Philippe Delagrange, Issy les Moulineaux (FR); Pierre Renard, Le Chesnay (FR); Caroline Bennejean, Charenton le Pont (FR); Jean Albert Boutin, Suresnes (FR); Valérie Audinot, Poissy (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 245 days.

(21) Appl. No.: 10/820,904

(22) Filed: Apr. 8, 2004

(65) Prior Publication Data

US 2004/0204449 A1 Oct. 14, 2004

(30) Foreign Application Priority Data

Apr. 9, 2003 (FR) .................................. 03 04381

(51) Int. Cl.
C07D 217/00 (2006.01)
A61K 31/47 (2006.01)

(52) U.S. Cl. ...................................... 514/307; 546/139
(58) Field of Classification Search ................ 546/139; 514/307
See application file for complete search history.

(56) References Cited

U.S. PATENT DOCUMENTS 5,116,986 A * 5/1992 Bomhard et al. ........... 546/141

OTHER PUBLICATIONS

Li, et al., *Drugs of the Future*, 2000, 25, 945-957.
Krause, et al., *Society for Neuroscience*, 1996, 22, No. 651.19, p. 1400.
Vacas, et al., *J. Pineal Research*, 1992, 13, 60-65.
Cagnacci, et al., *J. Pineal Research*, 1997, 22, 16-19.
Lagneux, et al., *Life Sciences*, 2000, 66, 503-509.
Brydon, et al., *Endocrinology*, 2001, 142, 4264-4271.
Bylesjö, et al., *International Journal of Eating Disorders*, 1996, 20, 443-446.
Ferrari, et al., *Biol. Psychiatry*, 1990, 27, 1007-1020.
Mazzucchelli, et al., *Molecular Brain Research*, 1996, 39, 117-126.
Brown, *CNS Drugs*, 1995, 3, 209-226.
Waldhauser, et al., *Psychopharmacology*, 1990, 100, 222-226.
Skene, et al., *Brain Research*, 1990, 528, 170-174.
Monteleone, et al., *Schizophrenia Research*, 1992, 7, 77-84.

Mc Intyre, et al., *Journal of Affective Disorders*, 1987, 12, 203-206.
Erlich, et al., *J. Neurosurg.*, 1985, 63, 321-341.
Maurizi, *Medical Hypotheses*, 27, 271-276.
Kopp, et al., *Behavioural Pharmacology*, 1999, 10, 73-83.
Kopp, et al., *Neuorpharmacology*, 2000, 39, 1865-1871.
Fanteck, et al., *Exp. Brain Res.*, 1995, 107, 321-325.
Rasmussen et al., *Endocrinology*, 1999, 140, 1009-1012.
Armstrong, et al., *Medical Hypotheses*, 1991, 34, 300-309.
O'Brien, et al., *Clinical Endocrinology*, 1986, 24, 359-364.
Motilva, et al., *Current Pharmaceutical Design*, 2001, 7, 909-931.
Tamarkin, et al., *Science*, 1985, 227, 714-720.
Chemineau, et al., *Rec. Med. Vet.*, 1991, 167, 227-239.
Xu, et al., *Drug Development Research*, 1996, 39, 167-173.
Règrigny, et al., *Am. J. Physiol.*, 1998, 275, 139-144.
Stankov, et al., *Neuroscience*, 1993, 52, 459-468.
Leone, et al., *Cephalalgia*, 1996, 16, 494-496.
Brun, et al., *Cephalalgia*, 1995, 15, 136-139.
Ying, et al., *Eur. J. of Pharmacology*, 1993, 246, 89-96.
Laudon, et al., *Journal of Clinical Endocrinology and Metabolism*, 1996, 81, 1336-1342.
Lissoni, et al., *British Journal of Cancer*, 1996, 74, 1466-1468.

* cited by examiner

Primary Examiner—Zinna N. Davis
(74) Attorney, Agent, or Firm—Hueschen and Sage

(57) ABSTRACT

The invention relatests compound of formula (I):

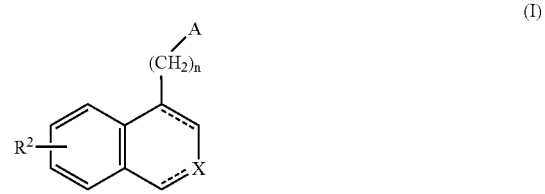

wherein:
n is 1, 2 or 3,
A represents a group

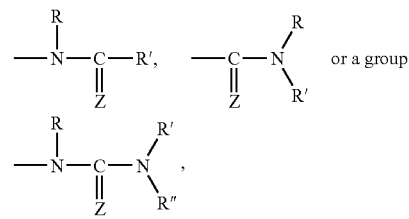

X represents N or NR$^1$,
R$^2$ represents an alkoxy, cycloalkyloxy or cycloalkylalkyloxy group.
and medicinal products containing the same which are useful in treading or in preventing melatoninergic disorder.

16 Claims, No Drawings

ISOQUINOLINE COMPOUNDS

FIELD OF THE INVENTION

The present invention relates to new isoquinoline compounds, to a process for their preparation and to pharmaceutical compositions containing them.

The compounds of the present invention are, in view of their original structure, new and have pharmacological properties that are of great interest in relation to melatoninergic receptors.

DESCRIPTION OF THE PRIOR ART

There are known from the literature isoquinoline compounds that are useful as vasodilators (U.S. Pat. No. 4,880, 817, U.S. Pat. No. 4,843,071, U.S. Pat. No. 4,822,800), or useful in the growth of plants (Czasopismo Techniezne (Krakow), 1992, 89 (1), 7–12), as tyrosine phosphatase modulators (WO 99 46268), or also useful in synthesis (Tetrahedron Letters, 2002, 43 (19), 3557–3560; Heterocycles, 2000, 52 (3), 1371–1383).

BACKGROUND OF THE INVENTION

In the last ten years, numerous studies have demonstrated the major role played by melatonin (N-acetyl-5-methoxytryptamine) in a large number of physiopathological phenomena and in the control of the circadian rhythm, but melatonin has a rather short half-life owing to the fact that it is rapidly metabolised. Great interest therefore lies in the possibility of making available to the clinician melatonin analogues that are metabolically more stable and have an agonist or antagonist character and of which the therapeutic effect may be expected to be superior to that of the hormone itself.

In addition to their beneficial action in respect of circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272), and analgesic properties (Pharmacopsychiat., 1987, 20, pp. 222–223), and also for the treatment of Parkinson's disease (J. Neurosurg. 1985, 63, pp. 321–341) and Alzheimer's disease (Brain Research, 1990, 528, pp. 170–174). The compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor sub-types that are capable of binding that hormone (Trends Pharmacol. Sci., 1995, 16, p. 50; WO 97.04094). It has been possible for some of those receptors to be located and characterised for different species, including mammals. In order to be able to understand the physiological functions of those receptors better, it is of great advantage to have available selective ligands. Moreover such compounds, by interacting selectively with one or another of those receptors, may be excellent medicaments for the clinician in the treatment of pathologies associated with the melatoninergic system, some of which have been mentioned above.

In addition to being new, the compounds of the present invention exhibit a very strong affinity for melatonin receptors and/or a selectivity for one or another of the melatoninergic receptor sub-types.

DETAILED DESCRIPTION OF THE INVENTION

The present invention relates, more especially, to the compounds of formula

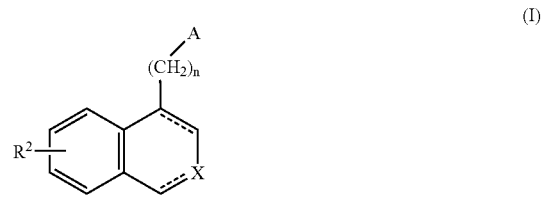

(I)

wherein:
n is 1, 2 or 3,
A represents a group

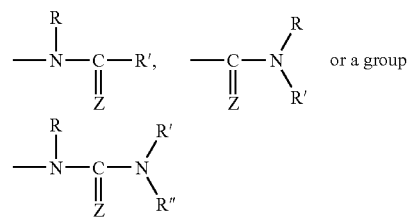

wherein:
Z represents a sulphur atom or an oxygen atom,
R and R", which may be identical or different, each represents a hydrogen atom or a linear or branched $(C_1-C_6)$alkyl group,
and R' represents a linear or branched $(C_1-C_6)$alkyl group, a linear or branched $(C_2-C_6)$alkenyl group, a linear or branched $(C_2-C_6)$alkynyl group, a $(C_3-C_8)$-cycloalkyl group, a $(C_3-C_8)$cycloalkyl-$(C_1-C_6)$alkyl group in which the alkyl moiety is linear or branched, an aryl group, an aryl-$(C_1-C_6)$alkyl group in which the alkyl moiety is linear or branched, a heteroaryl group or a heteroaryl-$(C_1-C_6)$alkyl group in which the alkyl moiety is linear or branched,
X represents a nitrogen atom or a group N—$R^1$ wherein $R^1$ represents a hydrogen atom or a linear or branched $(C_1-C_6)$alkyl group, a $(C_3-C_8)$cycloalkyl group, a $(C_3-C_8)$cyclo-alkyl-$(C_1-C_6)$alkyl group in which the alkyl moiety is linear or branched, an aryl group, an aroyl group, an aryl-$(C_1-C_6)$alkyl group in which the alkyl moiety is linear or branched, a heteroaryl group, a heteroaroyl group or a heteroaryl-$(C_1-C_6)$alkyl group in which the alkyl moiety is linear or branched,
$R^2$ represents a linear or branched $(C_1-C_6)$alkoxy group, a $(C_3-C_8)$cycloalkyloxy or $(C_3-C_8)$cycloalkyl-$(C_1-C_6)$ alkyloxy group in which the alkyloxy moiety is linear or branched, the representation ----- denotes that the bond is single or double, with the proviso that the valency of the atoms is respected, wherein:
"aryl" is to be understood as meaning a phenyl or naphthyl group, those groups being unsubstituted or substituted by from one to three identical or different groups selected from linear or branched ($C_1$–$C_6$)alkyl, linear or branched ($C_1$–$C_6$)alkoxy, OH, COOH, alkoxycarbonyl in which the alkoxy moiety is linear or branched, formyl, nitro, cyano, hydroxymethyl, amino (optionally substituted by one or two linear or branched ($C_1$–$C_6$) alkyl groups) and halogen atoms, "heteroaryl" is to be understood as meaning any mono- or bi-cyclic group that contains from 5 to 10 ring members and may contain from 1 to 3 hetero atoms selected from oxygen, sulphur and nitrogen, such as the groups furan, thiophene, pyrrole, imidazoline, pyridine, quinoline, isoquinoline, chroman, indole, benzothiophene or benzofuran, it being possible for those groups to be partially hydrogenated, unsubstituted or substituted by from one to three identical or different groups selected from linear or branched ($C_1$–$C_6$)alkyl, linear or branched ($C_1$–$C_6$)alkoxy, OH, COOH, alkoxycarbonyl in which the alkoxy moiety is linear or branched, formyl, nitro, cyano, amino (optionally substituted by one or two linear or branched ($C_1$–$C_6$)alkyl groups), hydroxymethyl and halogen atoms, to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The preferred values for n are 2 and 3.

Preferred compounds of the invention are compounds of formula (I) wherein:
n is 2 and A represents an —NHCOR' group and more especially an —NHCOR' group wherein R' represents a linear or branched ($C_1$–$C_6$)alkyl group, such as methyl, ethyl, propyl, isopropyl, butyl, isobutyl, pentyl or hexyl for example, or a ($C_3$–$C_8$)cycloalkyl group, such as cyclopropyl, cyclobutyl, cyclopentyl or cyclohexyl for example, n is 3 and A represents a —CONHR' group and more especially a —CONHR' group wherein R' represents a linear or branched ($C_1$–$C_6$)alkyl group, such as methyl, ethyl, propyl, isopropyl, butyl, isobutyl, pentyl or hexyl for example, or a ($C_3$–$C_8$)cycloalkyl group, such as cyclopropyl, cyclobutyl, cyclopentyl or cyclohexyl for example.

The preferred $R^2$ group is the alkoxy group and more especially the methoxy group.

X represents preferably a nitrogen atom or an $NR^1$ group wherein $R^1$ represents a cycloalkylalkyl group, an unsubstituted or substituted phenyl group, or a benzyl group in which the phenyl moiety is substituted or unsubstituted.

Even more preferably, the invention relates to the following compounds of formula (I):
N-[2-(6-methoxy-4-isoquinolinyl)ethyl]acetamide,
N-[2-(6-methoxy-4-isoquinolinyl)ethyl]butanamide,
N-[2-(6-methoxy-4-isoquinolinyl)ethyl]propanamide,
N-[2-(6-methoxy-4-isoquinolinyl)ethyl]cyclopropanecarboxamide,
4-(6-methoxy-4-isoquinolinyl)-N-methylbutanamide,
N-[2-(6-methoxy-2-phenyl-1,2,3,4-tetrahydro-4-isoquinolinyl)ethyl]acetamide,
N-[2-(2-benzyl-6-methoxy-1,2,3,4-tetrahydro-4-isoquinolinyl)]ethyl]acetamide,
N-{2-[2-(cyclopropylmethyl)-6-methoxy-1,2,3,4-tetrahydro-4-isoquinolinyl]-ethyl}acetamide.

The enantiomers, diastereoisomers and also addition salts with a pharmaceutically acceptable acid or base of the preferred compounds of the invention form an integral part of the invention.

The present invention relates also to a process for the preparation of compounds of formula (I), which process is characterised in that there is used as starting material a compound of formula (II):

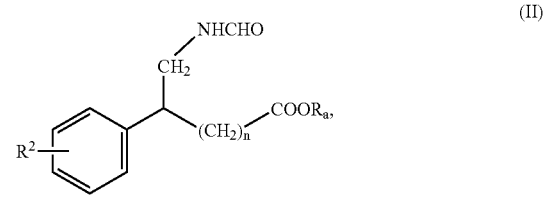

wherein $R^2$ and n are as defined for formula (I) and $R_a$ represents a linear or branched ($C_1$–$C_6$)alkyl group, which is subjected to the action of $POCl_3$ to obtain a compound of formula (III):

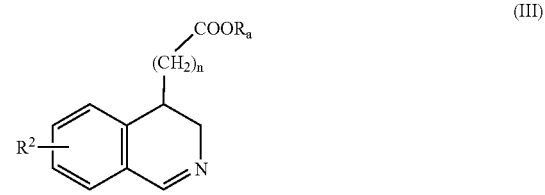

wherein $R^2$, n and $R_a$ are as defined hereinabove, which is placed:

in the presence of palladium-on-carbon to obtain a compound of formula (IV):

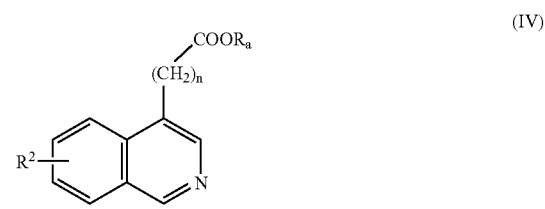

wherein $R^2$, n and $R_a$ are as defined hereinabove, or which is hydrogenated in the presence of palladium-on-carbon to yield a compound of formula (V):

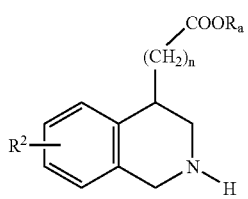
(V)

wherein R², n and R$_a$ are as defined hereinabove,
which compound of formula (V) is condensed with a compound of formula G—R'¹ wherein G represents a leaving group, such as a halogen atom, or a tert-butoxycarbonyl group, and R'¹ may have any of the meanings given for R¹ with the exception of a hydrogen atom, to yield a compound of formula (VI):

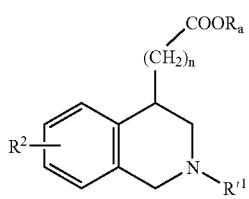
(VI)

wherein R², R'¹, n and R$_a$ are as defined hereinabove, the compounds of formulae (III) to (VI) constituting the compounds of formula (VII):

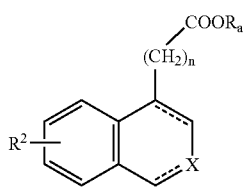
(VII)

wherein R², n and R$_a$ are as defined hereinabove and X and the representation ----- are as defined for formula (I), which is condensed with an amine of formula HNRR' wherein R and R' are as defined for formula (I) to obtain a compound of formula (I/a), a particular case of the compounds of formula (I):

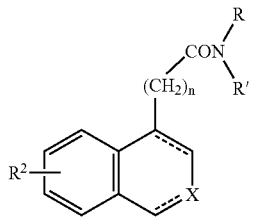
(I/a)

wherein R², R, R', X, n and the representation ----- are as defined hereinabove, or which compound of formula (VII) is subjected to a sequence of reactions conventional in organic chemistry to yield a compound of formula (VIII):

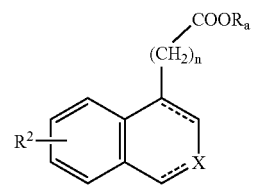
(VIII)

wherein R², X, n and the representation ----- are as defined hereinabove, which is:
either reacted with an acyl chloride ClCOR' or the corresponding mixed or symmetric anhydride wherein R' is as defined hereinabove to yield a compound of formula (I/b), a particular case of the compound of formula (I):

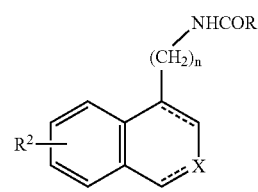
(I/b)

wherein R², R', X, n and the representation ----- are as defined hereinabove, optionally followed by the action of a compound of formula R'$_a$-J wherein R'$_a$ may have any of the meanings of R' and J represents a leaving group, such as a halogen atom or a tosyl group, to obtain a compound of formula (I/c), a particular case of the compounds of formula (I):

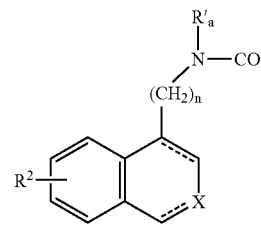
(I/c)

wherein R², R', R$_a$', X, n and the representation ----- are as defined hereinabove, or subjected to the action of a compound of formula (IX):

O=C=N—R'  (IX)

wherein R' is as defined hereinabove, optionally followed by the action of a compound of formula R'$_a$-J as defined hereinabove, to yield a compound of formula (I/d), a particular case of the compounds of formula (I):

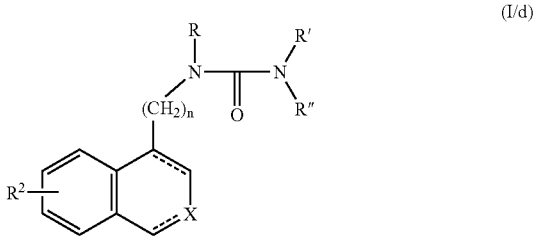

wherein R², R, R', n, X and the representation ---- are as defined hereinabove and R" is as defined for formula (I), it being possible for the compounds of formulae (I/a) to (I/d) to be subjected to the action of a thionisation agent, such as Lawesson's reagent for example, to yield a compound of formula (I/e), a particular case of the compounds of formula (I):

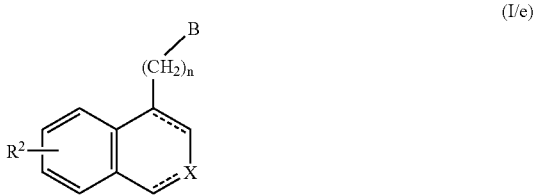

wherein R², n and the representation ---- are as defined hereinabove and B represents a C(S)NRR', N(R)C(S)R' or N(R)C(S)NR'R" group wherein R, R' and R" are as defined hereinabove, the compounds (I/a) to (I/e) constituting the totality of the compounds of formula (I), which compounds may be purified according to a conventional separation technique, are converted, if desired, into addition salts with a pharmaceutically acceptable acid or base, and are optionally separated into the isomers according to a conventional separation technique.

The starting compounds (II) are either commercially available or are easily obtainable by the person skilled in the art by conventional chemical reactions or by chemical reactions described in the literature.

The compounds of the invention and pharmaceutical compositions containing them prove to be useful in the treatment of disorders of the melatoninergic system.

A pharmacological study of the compounds of the invention has in fact demonstrated that they are non-toxic, have a high affinity for melatonin receptors and have substantial activity in respect of the central nervous system and in respect of microcirculation, enabling it to be established that the products of the invention are useful in the treatment of stress, sleep disorders, anxiety, severe depression, seasonal affective disorders, cardiovascular pathologies, pathologies of the digestive system, insomnia and fatigue due to jetlag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the products of the invention can be used in the treatment of sexual dysfunction, that they have ovulation-inhibiting and immunomodulating properties and that they lend themselves to use in the treatment of cancers.

The compounds will preferably be used in the treatment of severe depression, seasonal affective disorders, sleep disorders, cardiovascular pathologies, insomnia and fatigue due to jetlag, appetite disorders and obesity.

For example, the compounds will be used in the treatment of seasonal affective disorders and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those which are suitable for oral, parenteral, nasal, per- or transcutaneous, rectal, perlingual, ocular or respiratory administration, especially tablets or dragées, sublingual tablets, sachets, paquets, gelatin capsules, glossettes, lozenges, suppositories, creams, ointments, dermal gels and drinkable or injectable ampoules.

The dosage varies according to the sex, age and weight of the patient, the administration route, the nature of the therapeutic indication or any associated treatments, and ranges from 0.01 mg to 1 g per 24 hours in one or more administrations.

The following Examples illustrate the invention and do not limit it in any way. The following Preparations result in compounds of the invention or in synthesis intermediates for use in the preparation of compounds of the invention.

Preparation 1: Ethyl 4-(6-methoxy-3,4-dihydro-4-isoquinolinyl)butanoate hydrochloride Step A: Ethyl 5-cyano-5-(3-methoxyphenyl)pentanoate Two grams of (3-methoxyphenyl)acetonitrile and 1.5 ml of ethyl 4-bromobutyrate are dissolved in 50 ml of dimethylformamide at 0° C. Six hundred milligrams of 60% sodium hydride (600 mg; 15 mmol) are progressively added to the solution. The reaction mixture is stirred at ambient temperature for 4 hours, taken up in 100 ml of acidic water and extracted with ether. The organic phase is then dried over magnesium sulphate, filtered and evaporated under reduced pressure. The oil obtained is purified on a column (eluant:ether/cyclohexane 4/6) to yield the title product in the form of a yellow oil.

Step B: Ethyl 6-amino-5-(3-methoxyphenyl)hexanoate hydrochloride

The compound obtained in Step A (11.2 g; 43 mmol), dissolved beforehand in 150 ml of ethanol, is poured into an autoclave, and then Raney nickel is added (10% by weight). The mixture is then placed under hydrogen pressure (10 bars) and heated at 50° C. for 48 hours with stirring. After removing the Raney nickel by filtration, the organic phase is evaporated under reduced pressure. The residue obtained is taken up in ether, $HCl_{(g)}$ is bubbled into the solution, which is then stirred until precipitation occurs. The precipitate obtained is then suction-filtered off and recrystallised from toluene, and the title product is obtained in the form of a white solid.

Melting point: 104–106° C.

Step C: Ethyl 6-(formylamino)-5-(3-methoxyphenyl)hexanoate

The amine obtained in Step B, in the form of a base (6.4 g; 27 mmol), is dissolved in 60 ml of ethyl formate. The reaction mixture is heated at reflux for 6 hours with stirring and then evaporated under reduced pressure. The residue obtained is taken up in ether. The organic phase is then washed in succession with acidic water (1N HCl), water, and a 10% hydrogen carbonate solution, subsequently dried over magnesium sulphate, filtered and evaporated under reduced pressure to yield the title product in the form of a yellow oil.

Step D: Ethyl 4-(6-methoxy-3,4-dihydro-4-isoquinolinyl)butanoate hydrochloride The formaldehyde obtained in Step C (6.8 g; 23 mmol) is dissolved in 100 ml of acetonitrile, then the reaction mixture is heated to approximately 60° C. Phosphorus oxychloride (7 ml) is added to the solution, which is heated at reflux for 6 hours with stirring and then evaporated under reduced pressure. The residue obtained is taken up twice in ethanol and evaporated under reduced pressure, and is then taken up in water. The aqueous phase is washed with dichloromethane and then rendered alkaline with a saturated sodium hydrogen carbonate solution and extracted with dichloromethane. The organic phase is dried over magnesium sulphate, filtered and evaporated under reduced pressure. The oil obtained is taken un in ether saturated with $HCl_{(g)}$ and then evaporated under reduced pressure. The residue is taken up in toluene in the heated state and is stirred until precipitation occurs. The precipitate obtained is then suction-filtered off and the title product is obtained in the form of a white solid.

Melting point: 97–99° C.

Preparation 2: tert-Butyl 4-(2-aminoethyl)-6-methoxy-3,4-dihydro-2(1H)-isoquinolinecarboxylate

Step A: Methyl cyano(3-methoxyphenyl)acetate

Twenty five grams of (3-methoxyphenyl)acetonitrile are dissolved in 200 ml of anhydrous THF in an Erlermeyer ground-necked flask. 60% sodium hydride (8.88 g; 0.37 mol) is added to the solution and the reaction mixture is heated at reflux for 30 minutes with stirring. Dimethyl carbonate (58 ml; 0.6814 mol) is then added dropwise in the course of half an hour and the reaction mixture is subsequently heated at reflux for 2 hours with stirring. The reaction mixture is poured into cold and slightly acidic water. The aqueous phase is extracted with ether, and then the ethereal phase is washed with water before being evaporated. A solution of potassium carbonate (47.15 g; 0.34 mol ) is added to the oil obtained above. After stirring, the mixture is washed with ether. The ethereal phase obtained is rewashed with a solution of potassium carbonate (12.02 g; 0.08 mol). The two aqueous phases are combined, immediately acidified, and extracted with ether. The organic phase so obtained is washed with a 10% sodium hydrogen carbonate solution, dried over magnesium sulphate and evaporated under reduced pressure to yield the title product in the form of an orangey yellow oil.

Step B: Methyl 3-amino-2-(3-methoxyphenyl)propanoate hydrochloride

The compound obtained in Step A (34.32 g; 0.1672 mol) is dissolved in 150 ml of methanol. The solution is poured into an autoclave and then 50 ml of chloroform and platinium oxide (10% by weight) are added to the solution. The autoclave is placed under hydrogen pressure (60 bars) at ambient temperature and stirred magnetically for 24 hours. After removal of the catalyst by filtration, the solution is evaporated under reduced pressure. The oil obtained is taken up in ether. The precipitate formed is suction-filtered off and recrystallised from acetonitrile to yield the title product in the form of a white solid.

Melting point: 170–172° C.

Step C: Methyl 3-(formylamino)-2-(3-methoxyphenyl)propanoate

The compound obtained in Step B (20.25 g; 0.08 mol), in the form of a base, is dissolved in 130 ml of ethyl formate (1.81 mol). The reaction mixture is heated at reflux for 6 hours and then evaporated under reduced pressure. The oil obtained is taken up in ethyl acetate. The organic phase is washed with basic water ($NaHCO_3$), dried over magnesium sulphate, filtered and evaporated to yield the title product in the form of a yellow oil.

Step D: Methyl 6-methoxy-3,4-dihydro-4-isoquinolinecarboxylate hydrochloride The compound obtained in Step C (8.03 g; 0.03 mol) is dissolved in 100 ml of acetonitrile, and then the reaction mixture is heated to approximately 60° C. Phosphorus oxychloride (16 ml; 0.17 mol) is added to the solution, which is then heated at reflux for 6 hours with stirring and subsequently evaporated under reduced pressure. The residue obtained is taken up twice with methanol and evaporated under reduced pressure, and then taken up in a minimum of acetone. The precipitate formed is then suction-filtered off to yield the title product in the form of a white solid.

Melting point : 212–215° C.

Step E: Methyl 6-methoxy-1,2,3,4-tetrahydro-4-isoquinolinecarboxylate hydrochloride The compound obtained in Step D (9.21g), in the form of a base, is dissolved in 150 ml of methanol and then palladium-on-carbon (900 mg) is added to the solution. The reaction mixture is stirred at ambient temperature under hydrogen for 4 hours. After removal of the palladium-on-carbon by filtration, the organic phase is evaporated under reduced pressure. The oil obtained is taken up in ether saturated with HCl. The precipitate formed is suction-filtered off and recrystallised from acetonitrile to yield the title product in the form of a white solid.

Melting point: 191–193° C.

Step F: tert-Butyl 4-methyl 6-methoxy-3,4-dihydro-2,4(1H)-isoquinoline-dicarboxylate The compound obtained in Step E (4.02 g; 15 mmol) is suspended in 100 ml of dichloromethane and then triethylamine (6.6 ml) is added. When dissolution is complete, di-tert-butyl dicarbonate (4 g; 18 mmol) is added and the reaction mixture is stirred at ambient temperature for 30 minutes. The solution is poured into 100 ml of water and the excess of triethylamine is neutralised with acidic water (0.1N HCl). After separation, the aqueous phase is extracted with dichloromethane and the combined organic solutions are dried over magnesium sulphate, filtered and evaporated under reduced pressure. The title product is purified by chromatography on silica gel.

Colourless oil.

Step G: tert-Butyl 4-(hydroxymethyl)-6-methoxy-3,4-dihydro-2(1H)-isoquinoline-carboxylate Lithium aluminium hydride (5.62 g; 148 mmol) is suspended in 50 ml of anhydrous tetrahydrofuran. A solution of the compound obtained in Step F (11.9 g; 37 mmol), dissolved beforehand in 50 ml of anhydrous tetrahydrofuran, is then added dropwise. The reaction mixture is then stirred at ambient temperature for 2 hours. A minimum of sodium hydroxide solution (2N NaOH) is added to the reaction mixture until the evolution of gas has ceased in order to form the precipitates of lithium and aluminium hydroxides. The precipitates are then filtered off and washed with tetrahydrofuran. The organic phase is evaporated under reduced pressure. The title compound is purified by chromatography on silica gel.

Clear yellow oil.

Step H: tert-Butyl 6-methoxy-4-{[(methylsulphonyl)oxy]methyl}-3,4-dihydro-2(1H)-isoquinolinecarboxylate The compound obtained in Step G (10.5 g; 36 mmol) is dissolved in 150 ml of dichloromethane and then triethylamine (8.5 ml) is added. The solution is cooled to 0° C. and methanesulphonyl choride (4.8 ml; 62 mmol) is added dropwise. The reaction mixture is stirred at ambient temperature for 2 hours and then poured into 150 ml of water. The solution is extracted with dichloromethane, dried over magnesium sulphate, filtered and evaporated under reduced pressure. The title compound is purified by chromatography on silica gel.

Yellow oil.

Step I: tert-Butyl 4-(cyanomethyl)-6-methoxy-3,4-dihydro-2(1H)-isoquinolinecarboxylate Potassium cyanide (5.52 g; 85 mmol) is suspended in 50 ml of DMSO and the solution is heated to 80° C. The compound obtained in Step H (6.3 g; 17 mmol), dissolved beforehand in 50 ml of DMSO, is progressively added to the preceding solution, and then the reaction mixture is heated again at 80° C. for 30 minutes. The solution is poured into 150 ml of water and extracted three times with dichloromethane. The organic phase is then dried over magnesium sulphate, filtered and evaporated. The dark red oil obtained is purified by chromatography on silica gel (eluant:cyclohexane with the progressive addition of ethyl acetate until the proportions 8/2 are reached) and the solid obtained is recrystallised from cyclohexane to yield the title product in the form of a white solid.

Melting point: 75–77° C.

Step J: tert-Butyl 4-(2-aminoethyl)-6-methoxy-3,4-dihydro-2(1H)-isoquinolinecarboxylate The compound obtained in Step I (6.3 g; 21 mmol) is dissolved in 150 ml of methanol saturated with $NH_{3(g)}$. The solution is poured into an autoclave and Raney nickel (600 mg) is added. The reaction mixture is then stirred at 60° C. and under a hydrogen pressure of 50 bars for 6 hours. After removal of the catalyst by filtration, the solution is evaporated under reduced pressure and the title compound is obtained in the form of a colourless oil.

Preparation 3: (6-Methoxy4-isoquinolinyl)acetonitrile hydrochloride

Step A: Methyl 6-methoxy-4-isoquinolinecarboxylate hydrochloride

The compound obtained in Step D of Preparation 2 (1.56 g; 0.006 mol), in the form of a base, is dissolved in 10 ml of decahydronaphthalene and then activated palladium-on-carbon is added (10% by weight). The reaction mixture is heated at 130° C. for 24 hours with stirring. The catalyst is filtered off in the heated state and washed with ethyl acetate. After evaporation under reduced pressure, the oil obtained is taken up in an ethereal solution saturated with $HCl_{(g)}$. The precipitate formed is suction-filtered off and recrystallised from acetonitrile to yield the title product in the form of a white solid.

Melting point: 178–180° C.

Step B: (6-Methoxy-4-isoquinolinyl)methanol hydrochloride

The compound obtained in Step A (0.395 g; 0.0015 mol), in the form of a base, is dissolved in 200 ml of ether. Lithium aluminium hydride (0.14 g; 0.004 mol) is then progressively added while cooling the flask in ice. The reaction mixture is stirred at ambient temperature for one week. A minimum of 30% sodium hydroxide solution (a few drops) is added to the reaction mixture to form the precipitates of lithium and aluminium hydroxides. The precipitates are then filtered off and washed with ethyl acetate. The organic phase is dried over magnesium sulphate, filtered and evaporated under reduced pressure. The oil obtained is taken up in ether saturated with $HCl_{(g)}$. The precipitate formed is suction-filtered off and recrystallised from acetonitrile to yield the title product in the form of a white solid.

Melting point: 250–252° C.

Step C: 4-(Chloromethyl)-6-methoxyisoquinoline

The hydrochloride of the compound obtained in Step B (1.09 g; 0.005 mol) is suspended in 50 ml of chloroform. Thionyl chloride (2.80 ml; 0.04 mol) is added and then the reaction mixture is heated at reflux for 24 hours with stirring. After evaporation under reduced pressure, the residue obtained is taken up in ethyl ether. The precipitate formed is suction-filtered off and recrystallised from acetonitrile to yield the title compound in the form of a white solid.

Melting point: 256–257° C.

Step D: (6-Methoxy-4-isoquinolinyl)acetonitrile hydrochloride

The hydrochloride of the compound obtained in Step C (0.60 g; 0.0024 mol) is dissolved in 10 ml of a saturated aqueous potassium carbonate solution and 40 ml of dichloromethane. Tetrabutylammonium bromide (2 g; 0.006 mol) and potassium cyanide (0.80 g; 0.012 mol) are then added to the preceding solution. The reaction mixture is stirred at ambient temperature for 24 hours. The solution is extracted with dichloromethane, and the organic phase is washed with water, dried over magnesium sulphate, filtered and evaporated. The oil obtained is taken up in acetone and in ether saturated with $HCl_{(g)}$. The precipitate formed is suction-filtered off and recrystallised from toluene/cyclohexane, 5/5, to yield the title compound in the form of a yellow solid.
Melting point : 114–115° C.

Preparation 4: tert-Butyl 4-(aminomethyl)-6-methoxy-3,4-dihydro-2(1H)-isoquinolinecarboxylate Step A: tert-Butyl 6-methoxy-4-{[(methylsulphonyl)oxy]methyl}-3,4-dihydro-2(1H)-isoquinolinecarboxylate The procedure is as in Steps A to H of Preparation 2.

Step B: tert-Butyl 4-(azidomethyl)-6-methoxy-3,4-dihydro-2(1H)-isoquinolinecarboxylate Sodium azide (1.12 g) is suspended in 40 ml of DMF and the solution is heated to 80° C. The compound obtained in Step A (1.6 g), dissolved beforehand in 10 ml of DMF, is progressively added to the preceding solution, and then the reaction mixture is heated again at 80° C. for from 2 to 3 hours.
The solution is poured into 150 ml of water and extracted three times with ethyl acetate. The organic phase is then dried over magnesium sulphate, filtered and evaporated. The dark red oil obtained is purified by chromatography on silica gel (eluant: cyclohexane with the progressive addition of ethyl acetate until the proportions 5/5 are reacehd) to yield the title product in the form of a colourless oil.

Step C: tert-Butyl 4-(aminomethyl)-6-methoxy-3,4-dihydro-2(1H)-isoquinolinecarboxylate The compound obtained in Step B (1.14 g) is dissolved in 100 ml of methanol and then palladium-on-carbon (120 mg) is added to the solution. The reaction mixture is stirred at ambient temperature and under hydrogen for 3 hours.
After removal of the palladium-on-carbon by filtration, the organic phase is evaporated under reduced pressure. The residue obtained is purified by chromatography on silica gel (eluant: cyclohexane with the progressive addition of ethyl acetate until the proportions 5/5 are reached) to yield the title product in the form of a colourless oil.

EXAMPLE 1

4-(6-methoxy-3,4-dihydro-4-isoquinolinyl)-N-methylbutanamide

The compound obtained in Preparation 1 (41 mmol), in the form of a base, is dissolved in 10 ml of ethanol. 60 ml of aqueous methylamine are added and the reaction mixture is stirred at ambient temperature for 12 hours. After evaporation under reduced pressure, the filtrate is taken up in 50 ml of water and extracted with dichloromethane. The organic phase is washed with water, dried over magnesium sulphate, filtered and evaporated under reduced pressure. The title product is obtained after chromatography of the resulting oil on silica gel.
Yellow oil.

EXAMPLE 2

4-(6-Methoxy-1,2,3,4-tetrahydro-4-isoquinolinyl)-N-methylbutanamide

The compound obtained in Example 1 (54 mmol), in the form of a base, is dissolved in 50 ml of methanol and then palladium-on-carbon (150 mg) is added to the solution. The reaction mixture is stirred at ambient temperature and under hydrogen for 4 hours. After removal of the palladium-on-carbon by filtration, the organic phase is evaporated under reduced pressure. The oil obtained is purified by chromatography on silica gel to yield the title product in the form of a yellow oil.

EXAMPLE 3

4-(6-methoxy-4-isoquinolinyl)-N-methylbutanamide

Step A: Ethyl 4-(6-methoxy-4-isoquinolinyl)butanoate hydrochloride

The compound obtained in Preparation 1 (1.6 g; 5 mmol) is dissolved, with the application of heat, in 20 ml of toluene containing triethylamine (0.9 ml) and absolute ethanol (2 ml). Palladium-on-carbon (300 mg) is added to the reaction mixture, which is then heated at reflux for 24 hours with stirring. After removal of the palladium-on-carbon by filtration, the organic phase is evaporated under reduced pressure. The residue obtained is purified by chromatography on silica gel (eluant: dichloromethane with the progressive addition of methanol). The oil obtained is converted to hydrochloride form and then the precipitate formed is recrystallised from acetonitrile.
Melting point: 190–192° C.

Step B: 4-(6-methoxy-4-isoquinolinyl)-N-methylbutanamide

The compound obtained in Step A (2.2 g; 7 mmol) is dissolved in 30 ml of methylamine (40% in water) and the mixture is heated at reflux for 3 hours with stirring. The reaction mixture is taken up in 50 ml of water and extracted with ether. The organic phase is washed with water, dried over magnesium sulphate, filtered and evaporated under reduced pressure. The oil obtained is purified by chromatography on silica gel (eluant: dichloromethane with the progressive addition of methanol). The oil obtained is evaporated under reduced pressure and the precipitate so formed is recrystallised from toluene to yield the title product in the form of a white solid.
Melting point: 117–119° C.

Elemental Microanalysis:

|  | C % | H % | N % |
|---|---|---|---|
| calculated | 69.74 | 7.02 | 10.84 |
| found | 69.64 | 7.22 | 10.83 |

EXAMPLE 4

N-[2-(6-methoxy-1,2,3,4-tetrahydro-4-isoquinolinyl)ethyl]acetamide hydrochloride The compound obtained in Step I of Preparation 2 (6 g; 20 mmol) is dissolved in 100 ml of acetic anhydride and then the solution is poured into an autoclave. Raney nickel (600 mg) is then added to the solution and the reaction mixture is stirred at 60° C. and under a hydrogen pressure of 50 bars for 6 hours. After removal of the catalyst by filtration, the solution is evaporated under reduced pressure. The orange residue obtained is taken up in a 10% sodium hydroxide solution and stirred for 15 minutes, and then extracted with ethyl acetate (3 times). The organic phase is washed once with water, dried over magnesium sulphate, filtered and evaporated under reduced pressure. The oil obtained is taken up in 50 ml of methanol. Hydrogen chloride gas is bubbled into the solution, which is then stirred for 24 hours with a CaCl$_2$ guard. The solution is evaporated under reduced pressure and the precipitate so obtained is recrystallised from acetonitrile to yield the title product in the form of a white solid.

Melting point: 182–184° C.

EXAMPLE 5

N-[2-(6-methoxy-1,2,3,4-tetrahydro-4-isoquinolinyl)ethyl]propanamide hydrochloride The compound obtained in Preparation 2 and 2 equivalents of potassium carbonate are dissolved in a 3/2 ethyl acetate/water mixture. Propanoyl chloride (2 equivalents) is then added dropwise to the solution. The reaction mixture is stirred at ambient temperature for one hour. After separation of the phases, the organic phase is washed with water, dried over magnesium sulphate, filtered and evaporated under reduced pressure. The oil obtained is purified by chromatography on silica gel (eluant ethyl acetate/cyclohexane 5/5). The oil obtained is taken up in methanol. Hydrogen chloride gas is bubbled into the solution, which is then stirred for 24 hours with a CaCl$_2$ guard. The solution is evaporated under reduced pressure and the title compound is obtained in the form of a white solid.

Melting point: 161–163° C.

EXAMPLE 6

N-[2-(6-methoxy-1,2,3,4-tetrahydro-4-isoquinolinyl)ethyl]butanamide hydrochloride The title compound is obtained by the same procedure as in Example 5, with the replacement of propanoyl chloride by butanoyl chloride.

Very hygroscopic white solid.

EXAMPLE 7

N-[2-(6-methoxy-1,2,3,4-tetrahydro-4-isoquinolinyl)ethyl]cyclopropane-carboxamide hydrochloride The title compound is obtained by the same procedure as in Example 5, with the replacement of propanoyl chloride by cyclopropylcarboxylic acid chloride.

White solid.

Melting point: 215–217° C.

EXAMPLE 8

N-[2-(6-methoxy-1,2,3,4-tetrahydro-4-isoquinolinyl)ethyl]cyclobutane-carboxamide hydrochloride The title compound is obtained by the same procedure as in Example 5, with the replacement of propanoyl chloride by cyclobutylcarboxylic acid chloride.

White solid.

Melting point: 130–132° C.

EXAMPLE 9

N-[2-(6-methoxy-4-isoquinolinyl)ethyl]acetamide hydrochloride

The compound obtained in Preparation 3 (0.30 g; 0.0015 mol), in the form of a base, dissolved beforehand in 10 ml of acetic anhydride, is poured into an autoclave and then Raney nickel is added (10% by weight). The mixture is then placed under hydrogen pressure (60 bars) and heated at 60° C. for 6 hours with stirring. After removal of the Raney nickel by filtration, the organic phase is taken up in 10% sodium hydroxide solution at ambient temperature and stirred magnetically for 15 minutes. The solution is extracted with ethyl acetate, the organic phase is washed with brine, dried over magnesium sulphate, filtered and evaporated under reduced pressure. The oil obtained is purified on a column (eluant dichloromethane with the progressive addition of methanol until the proportions 9/1 are reached). The purified oil is taken up in ether saturated with HCl$_{(g)}$. The precipitate formed is suction-filtered off and recrystallised from ethanol to yield the title product in the form of a white solid.

Melting point: 212–214° C.

EXAMPLE 10

N-[2-(6methoxy-4-isoquinolinyl)ethyl]propanamide hydrochloride

The compound of Example 5 is dissolved in a minimum of methanol with the application of heat and then diluted with toluene. 1.5 equivalents of triethylamine are then added to the solution, and the reaction mixture is subsequently heated at reflux in the presence of palladium-on-carbon (10% by weight) for 3 hours. After removal of the catalyst by filtration, the solution is evaporated under reduced pressure. The oil obtained is purified by chromatography on silica gel (eluant dichlormethane/methanol 9/1). The purified oil is taken up in ether saturated with HCl$_{(g)}$ and stirred until a precipitate is obtained. The precipitate so formed is suction-filtered off and placed under vacuum in a dessicator. The title product is obtained in the form of a white solid.

Melting point: 233–235° C.

EXAMPLE 11

N-[2-(6-methoxy-4-isoquinolinyl)ethyl]butanamide hydrochloride

The title compound is obtained according to the same procedure as in Example 10 starting from the compound obtained in Example 6.

Melting point: 195–197° C.

EXAMPLE 12

N-[2-(6-methoxy-4-isoquinolinyl)ethyl]cyclopropanecarboxamide hydrochloride

The title compound is obtained according to the same procedure as in Example 10 starting from the compound obtained in Example 7.

Melting point: 226–228° C.

EXAMPLE 13

N-[2-(6methoxy-2-phenyl-1,2,3,4-tetrahydro-4-isoquinolinyl)ethyl]-acetamide hydrochloride The compound obtained in Example 4 (460 mg; 1.8 mmol), in the form of a base, is suspended in 30 ml of dichloromethane. Triphenylbismuth (900 mg; 2 mmol) and copper acetate $Cu(OAc)_2$ (190 mg; 0.95 mmol) are then added. The reaction mixture is placed under argon and stirred magnetically for 18 hours at ambient temperature. The mixture is filtered, taken up in water and extracted with ethyl acetate. The organic phase is dried over magnesium sulphate, filtered and evaporated under reduced pressure. The residue obtained is purified by chromatography on silica gel (eluant ethyl acetate/cyclohexane 2/8). The purified oil is taken up in ether saturated with $HCl_{(g)}$ and stirred until a precipitate is obtained, which precipitate is then suction-filtered off and placed under a vacuum in a dessicator to yield the title product in the form of a white solid.

Melting point : 83–85° C.

EXAMPLE 14

N-[2-(2-benzyl-6methoxy-1,2,3,4-tetrahydro-4-isoquinolinyl)ethyl]-acetamide

The compound obtained in Example 4 (740 mg; 2.5 mmol) and potassium carbonate (720 mg; 5 mmol) are suspended in 20 ml of DMF, and then benzyl bromide (0.37 ml; 3 mmol) is added to the solution. The reaction mixture is heated at 125° C. for 4 hours with stirring. The solution is poured into 50 ml of water, acidified with 6N HCl and washed with ethyl acetate. The aqueous phase is then rendered alkaline with potassium carbonate and extracted with dichloromethane. The organic phase is dried over magnesium sulphate, filtered and evaporated under reduced pressure. The residue so obtained is purified by chromatography on silica gel (eluant: dichloromethane with the progressive addition of methanol until the proportions 9/1 are reached). The purified oil precipitates. The precipitate so formed is recrystallised from a 7/3 toluene/cyclohexane mixture to yield the title product in the form of a white solid.

Melting point: 123–125° C.

EXAMPLE 15

N-{2-[2-(3-formylphenyl)-6-methoxy-1,2,3,4-tetrahydro-4-iso-quinolinyl]ethyl}acetamide Copper acetate $Cu(OAc)_2$ (960 mg; 5 mmol) and triethylamine (1.5 ml; 10.5 mmol) are suspended in 60 ml of dichloromethane. The compound of Example 4 (1 g; 3.5 mmol), 3-formylphenylboronic acid (1.05 g; 7 mmol) and molecular sieve are then added in succession and progressively to the solution. The reaction mixture is stirred at ambient temperature for 2 hours. The mixture is filtered, washed with water, dried over magnesium sulphate, filtered and evaporated under reduced pressure. The residue obtained is purified by chromatography on silica gel (eluant: dichloromethane with the progressive addition of methanol until the proportions 9/1 are reached) to yield the title product in the form of a yellow oil.

EXAMPLE 16

N-[2-(6-methoxy-2-methyl-1,2,3,4-tetrahydro-4-isoquinolinyl)ethyl]-acetamide hydrochloride Formic acid (0.55 ml) and 37% formaldehyde (0.6 ml) are added at 0° C. to the compound obtained in Example 4 (1.8 g; 7.2 mmol) in the form of a base. The reaction mixture is heated at 80° C. for 24 hours with stirring. After having cooled the reaction mixture to 0° C., 10 ml of 6N HCl are added. The mixture is then washed with ether, rendered alkaline with 2N NaOH and extracted with ether. The organic phase is dried over magnesium sulphate, filtered and evaporated under reduced pressure. The yellow oil so obtained is purified by chromatography on silica gel (eluant: dichloromethane with the progressive addition of methanol until the proportions 9/1 are reached). The purified oil is taken up in ether saturated with $HCl_{(g)}$ and stirred until a precipitate is obtained, which precipitate is then suction-filtered off and placed under a vacuum in a dessicator to yield the title product in the form of a very hygroscopic white solid.

Melting point: 59–61° C.

EXAMPLE 17

N-{2-[2-(Cyclopropylmethyl)-6-methoxy-1,2,3,4-tetrahydro-4-isoquinolinyl]ethyl}acetamide hydrochloride The compound obtained in Example 4 (1.03 g) and potassium carbonate (1.25 g) are suspended in 50 ml of acetone. The solution is stirred at ambient temperature for 10 minutes, and then methylcyclopropane bromide (0.36 ml) is added to the solution. The reaction mixture is stirred at ambient temperature for 12 hours.

The potassium carbonate is filtered off and the recovered solution is evaporated. The residue is taken up in water and the aqueous phase is extracted with ether. The organic phase is dried over magnesium sulphate, filtered and evaporated under reduced pressure. The residue so obtained is purified by chromatography on silica gel (eluant: dichloromethane with the progressive addition of methanol until the proportions 9/1 are reached).

The purified oil is taken up in ether saturated with $HCl_{(g)}$ and stirred until a precipitate is obtained, which precipitate is then suction-filtered off and placed under a vacuum in a dessicator to yield the title product in the form of a hygroscopic white solid.

Melting point: <50° C.

EXAMPLE 18

N-[(6-Methoxy-1,2,3,4-tetrahydro-4-isoquinolinyl)methyl]acetamide hydrochloride

The compound obtained in Preparation 4 (0.77 g) and potassium carbonate (1.8 g) are dissolved in 50 ml of a 1/1 dichloromethane/water mixture. Acetyl chloride (0.47 ml) is then added dropwise to the solution. The reaction mixture is stirred at ambient temperature for 2 hours.

After separation of the phases, the organic phase is washed with water, dried over magnesium sulphate, filtered and evaporated under reduced pressure.

The oil obtained is taken up in methanol. Hydrogen chloride gas is bubbled into the solution, which is then stirred with a $CaCl_2$ guard for 24 hours, the deprotection time. The solution is evaporated under reduced pressure and the precipitate obtained is recrystallised from acetonitrile to yield the title product in the form of a white solid.

Melting point: 246–248° C.

Pharmacological Study

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (the dose that causes the death of 50% of the animals) was evaluated and demonstrated the low toxicity of the compounds of the invention.

EXAMPLE B

Forced Swimming Test

The compounds of the invention are tested in a behavioural model, the forced swimming test.

The apparatus is a Plexiglas cylinder filled with water. The animals are tested individually for a session of 6 minutes. At the beginning of each test, the animal is placed in the centre of the cylinder. The period of immobility is recorded. Each animal is judged to be immobile when it ceases to struggle and remains immobile on the surface of the water only making movements that allow it to keep its head out of the water.

After administration 40 minutes before the beginning of the test, the compounds of the invention significantly reduce the period of immobility, demonstrating the anti-depressant activity of the compounds of the invention. In particular, the compound of Example 9, administered at 2.5 mg/kg per os, causes the duration of immobility to be reduced from 102 seconds (control) to 57 seconds. The compound of Example 3, administered at 25 mg/kg per os, causes the duration of immobilisation to be reduced from 129 seconds (control) to 60 seconds.

EXAMPLE C

Study of Binding to Melatonin Receptors $MT_1$ and $MT_2$

The $MT_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities ($K_i$) of the compounds tested to be determined.

Thus, the $K_i$ values found for the compounds of the invention show binding for one or the other of the receptor sub-types $MT_1$ or $MT_2$, those values being $\leq 10$ µM.

In particular, the compound of Example 9 has a $K_i$ ($MT_1$) of $9.12 \times 10^{-9}$M and a $K_i(MT_2)$ of $2.16 \times 10^{-9}$M; the compound of Example 3 has a $K_i(MT_1)$ of $3.8 \times 10^{-9}$M and a $K_i(MT_2)$ of $2.6 \times 10^{-9}$M; the compound of Example 10 has a $K_i(MT_1)$ of $4.26 \times 10^{-9}$M and a $K_i(MT_2)$ of $1.14 \times 10^{-9}$M.

EXAMPLE D

Action of the Compounds of the Invention on the Circadian Rhythms of Locomotive Activity of the Rat The implication of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness), are evaluated.

Experimental Protocol

One-month-old male rats are subjected, as soon as they arrive at the laboratory, to a light cycle of 12 hours of light per 24 hours (LD 12:12).

After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:
  influence of the light rhythm on the rhythms of activity,
  disappearance of the influence on the rhythms in permanent darkness,
  influence by the daily administration of the compound; transitory or durable effect.

A software package makes it possible:
  to measure the duration and intensity of the activity, the period of the rhythm of the animals during free course and during treatment,
  to demonstrate by spectral analysis the existence of circadian and non-circadian (for example ultradian) components, where present.

Results

The compounds of the invention clearly appear to have a powerful action on the circadian rhythm via the melatoninergic system.

EXAMPLE E

Light/Dark Cages Test

The compounds of the invention are tested in a behavioural model, the light/dark cages test, which enables the anxiolytic activity of the compounds to be revealed.

The equipment comprises two polyvinyl boxes covered with Plexiglas. One of the boxes is in darkness. A lamp is placed above the other box, yielding a light intensity of approximately 4000 lux at the centre of the box. An opaque plastics tunnel separates the light box from the dark box. The animals are tested individually for a session of 5 minutes. The floor of each box is cleaned between each session. At the start of each test, the mouse is placed in the tunnel, facing the dark box. The time spent by the mouse in the illuminated box and the number of passages through the tunnel are recorded after the first entry into the dark box.

After administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of the Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. The stimulation of the receptors can induce either vasoconstriction or dilation depending upon the arterial segment studied.

Protocol

One-month-old rats are accustomed to a light/dark cycle of 12h/12h during a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 μM). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of caudal arteries pre-constricted by phenylephrine.

EXAMPLE G

Pharmaceutical Composition: Tablets

| | |
|---|---|
| 1000 tablets each containing a dose of 5 mg of N-[2-(6-methoxy-4-isoquinolinyl)-ethyl]acetamide hydrochloride (Example 9) | 5 g |
| wheat starch | 20 g |
| maize starch | 20 g |
| lactose | 30 g |
| magnesium stearate | 2 g |
| silica | 1 g |
| hydroxypropyl cellulose | 2 g |

The invention claimed is:

1. A compound selected from those of formula (I):

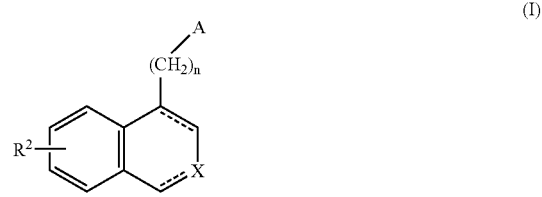

(I)

wherein:
n is 1, 2 or 3,
A represents

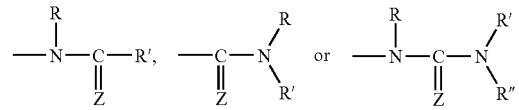

wherein:
Z represents sulphur or oxygen,
R and R", which may be identical or different, each represents hydrogen or linear or branched ($C_1$–$C_6$) alkyl,
and R' represents linear or branched ($C_1$–$C_6$)alkyl; linear or branched ($C_2$–$C_6$)alkenyl; linear or branched ($C_2$–$C_6$); ($C_3$–$C_8$)cycloalkyl; ($C_3$–$C_8$)cycloalkyl($C_1$–$C_6$)alkyl in which the alkyl moiety is linear or branched; aryl; aryl-($C_1$–$C_6$)alkyl in which the alkyl moiety is linear or branched; heteroaryl; or heteroaryl($C_1$–$C_6$)alkyl in which the alkyl moiety is linear or branched,
X represents nitrogen or N—$R^1$ wherein $R^1$ represents hydrogen or linear or branched ($C_1$–$C_6$)alkyl, ($C_3$–$C_8$) cycloalkyl, ($C_3$–$C_8$)cycloalkyl-($C_1$–$C_6$)alkyl in which the alkyl moiety is linear or branched, aryl, aroyl, aryl-($C_1$–$C_6$)alkyl in which the alkyl moiety is linear or branched, heteroaryl, heteroaroyl or heteroaryl-($C_1$–$C_6$)alkyl in which the alkyl moiety is linear or branched,
$R^2$ represents linear or branched ($C_1$–$C_6$)alkoxy, ($C_3$–$C_8$) cycloalkyloxy or ($C_3$–$C_8$)cycloalkyl-($C_1$–$C_6$)alkyloxy in which the alkyloxy moiety is linear or branched,
- - - - - the representation denotes that the bond is single or double, with the proviso that the valency of the atoms is respected,
its enantiomers and diastereoisomers, and addition salts thereof with a pharmaceutically acceptable acid or base, it being understood that:
- "aryl" may be "phenyl" or "naphthyl", each of those groups being optionally substituted by from one to three identical or different groups selected from linear or branched ($C_1$–$C_6$)alkyl, linear or branched ($C_1$–$C_6$)alkoxy, OH, COOH, alkoxycarbonyl in which the alkoxy moiety is linear or branched, formyl, nitro, cyano, hydroxymethyl, amino (optionally substituted by one or two linear or branched ($C_1$–$C_6$)alkyl) and halogen,
- "heteroaryl" may be any mono- or bi-cyclic group that contains from 5 to 10 ring members and may contain from 1 to 3 hetero atoms selected from oxygen, sulphur and nitrogen, each of those groups being optionally partially hydrogenated and optionally substituted by from one to three identical or different groups selected from linear or branched ($C_1$–$C_6$)alkyl, linear or branched ($C_1$–$C_6$)alkoxy, OH, COOH, alkoxycarbonyl in which the alkoxy moiety is linear or branched, formyl, nitro, cyano, amino (optionally substituted by one or two linear or branched ($C_1$–$C_6$)alkyl), hydroxymethyl and halogen.

2. A compound of claim 1 wherein n is 2 and A represents —NHCOR'.

3. A compound of claim 1 wherein n is 3 and A represents CONHR'.

4. A compound of claim 1 wherein $R^2$ represents methoxy.

5. A compound of claim 1 wherein X represents nitrogen.

6. A compound of claim 1 wherein X represents NPh or NBz.

7. A compound of claim 1 which is N-[2-(6-methoxy-4-isoquinolinyl)ethyl]acetamide, and its addition salts with a pharmaceutically acceptable acid.

8. A compound of claim 1 which is N-[2-(6-methoxy-4-isoquinolinyl)ethyl]butanamide, and its addition salts with a pharmaceutically acceptable acid.

9. A compound of claim 1 which is N-[2-(6-methoxy-4-isoquinolinyl)ethyl]propanamide, and its addition salts with a pharmaceutically acceptable acid.

10. A compound of claim 1 which is N-[2-(6-methoxy-4-isoquinolinyl)ethyl]cyclopropanecarboxamide, and its addition salts with a pharmaceutically acceptable acid.

11. A compound of claim 1 which is 4-(6-methoxy-4-isoquinolinyl)-N-methylbutanamide, and its addition salts with a pharmaceutically acceptable acid.

12. A compound of claim 1 which is N-[2-(6-methoxy-2-phenyl-1,2,3,4-tetrahydro-4-isoquinolinyl)ethyl]acetamide, and its addition salts with a pharmaceutically acceptable acid.

13. A compound of claim 1 which is N-[2-(2-benzyl-6-methoxy-1,2,3,4-tetrahydro-4-isoquinolinyl)ethyl]acetamide, and its addition salts with a pharmaceutically acceptable acid.

14. A compound of claim 1 which is N-{2-[2-(cyclopropylmethyl)-6-methoxy-1,2,3,4-tetrahydro-4-isoquinolinyl]ethyl}acetamide, and its addition salts with a pharmaceutically acceptable acid.

15. A pharmaceutical composition comprising as active principle an effective amount of a compound of claim 1 together with one or more pharmaceutically acceptable excipients or vehicles.

16. A method for treating a living animal body afflicted with a disorder selected from depression, seasonal affective disorders, schizophrenia, panic attacks, psychotic disorders, and senile dementia, comprising the step of administering to the animal body an amount of a compound of claim 1 which is effective for alleviation of the disorder.

* * * * *

UNITED STATES PATENT AND TRADEMARK OFFICE
CERTIFICATE OF CORRECTION

| | | |
|---|---|---|
| PATENT NO. | : 7,214,689 B2 | Page 1 of 1 |
| APPLICATION NO. | : 10/820904 | |
| DATED | : May 8, 2007 | |
| INVENTOR(S) | : Sophie Poissonnier-Durieux et al. | |

It is certified that error appears in the above-identified patent and that said Letters Patent is hereby corrected as shown below:

Title page, Item (56) References Cited: Maurizi, Medical Hypotheses, 27, 271-267."
Should be -- Maurizi, Medical Hypotheses, 1988, 27, 271-267.--.

Column 22, Line 46: "$(C_2\text{-}C_6)$" should be -- $(C_2\text{-}C_6)$alkynyl --.

Signed and Sealed this

Twenty-seventh Day of November, 2007

JON W. DUDAS
*Director of the United States Patent and Trademark Office*